(12) United States Patent
Smith et al.

(10) Patent No.: US 7,045,287 B2
(45) Date of Patent: May 16, 2006

(54) METHOD FOR CONTACTING FLUID COMPONENTS WITH MOIETIES ON A SURFACE

(75) Inventors: Douglas H. Smith, Burlingame, CA (US); Gary B. Gordon, Saratoga, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 124 days.

(21) Appl. No.: 09/792,169

(22) Filed: Feb. 21, 2001

(65) Prior Publication Data

US 2002/0001803 A1    Jan. 3, 2002

Related U.S. Application Data

(63) Continuation of application No. 09/357,440, filed on Jul. 20, 1999, now abandoned.

(51) Int. Cl.
*C12Q 1/68* (2006.01)
*C12M 3/00* (2006.01)
*G01N 33/566* (2006.01)
*C07K 1/00* (2006.01)
*C07H 21/02* (2006.01)

(52) U.S. Cl. ............ 435/6; 435/287.2; 436/501; 436/94; 536/23.1; 536/24.31; 530/350; 530/387.1

(58) Field of Classification Search ............ 435/6, 435/287.2; 436/94; 536/23.1, 24.71, 24.23
See application file for complete search history.

(56) References Cited

U.S. PATENT DOCUMENTS 4,287,061 A * 9/1981 Sutherland ............ 210/198.2
5,200,313 A * 4/1993 Carrico ............ 435/6
5,230,866 A * 7/1993 Shartle et al. ............ 422/103
5,804,384 A    9/1998 Muller et al.
5,891,630 A * 4/1999 Eggers et al. ............ 435/6

(Continued)

OTHER PUBLICATIONS

Zhang et al., Bioinformatics, vol. 19, No. 1, 2003, pp. 14-21.*

(Continued)

*Primary Examiner*—Bradley L. Sisson
(74) *Attorney, Agent, or Firm*—Gordon M. Stewart

(57) ABSTRACT

An improved method is provided for conducting chemical or biochemical reactions on a substrate surface in which the reactions take place in an enclosed chamber between components of a fluid and molecular moieties present on an interior surface of the chamber, wherein the improvement involves mixing the fluid during the reactions and maximizing contact between the fluid's components and the entirety of the reactive interior surface by (a) applying centrifugal force to the chamber and simultaneously (b) rotating the chamber about an axis thereof. The improved method is particularly advantageous in the context of a hybridization assay in which molecular components within a sample fluid hybridize to surface-bound molecular probes (e.g., as may be present in a spatially defined and physically addressable array) within a hybridization chamber, and wherein process and device parameters (e.g., sample volume, chamber volume, temperature, number of parts and materials, and the like) are critical. The invention enables use of a very small sample volume without need for a correspondingly small device, minimizes contamination (device components are disposable and the number of parts with which a fluid comes into contact is minimal), and further enables heating of the device prior to contacting the reactive surface with a sample fluid.

34 Claims, 5 Drawing Sheets

U.S. PATENT DOCUMENTS

| | | | |
|---|---|---|---|
| 5,919,629 A | | 7/1999 | Hillman et al. |
| 6,077,674 A | * | 6/2000 | Schleifer et al. ............... 435/6 |
| 6,309,875 B1 | | 10/2001 | Gordon |
| 2002/0012910 A1 | * | 1/2002 | Weiss et al. .................... 435/6 |
| 2002/0119455 A1 | * | 8/2002 | Chan .............................. 435/6 |

OTHER PUBLICATIONS

Nikiforov et al., Analytical Biochemistry, vol. 227, 1995, pp. 201-209.*

A. Diagger and Co., Laboratory Equipment and Supplies Catalog, 1999, p. 538.*

* cited by examiner

METHOD FOR CONTACTING FLUID COMPONENTS WITH MOIETIES ON A SURFACE

CROSS REFERENCE TO RELATED APPLICATIONS

This application is a continuation of application Ser. No. 09/357,440 filed for "IMPROVED METHOD FOR CONDUCTING CHEMICAL, OR BIOCHEMICAL REACTIONS ON A SUBSTRATE" by Smith on Jul. 20, 1999, now abandoned, from which priority is claimed under 35 U.S.C. 120.

TECHNICAL FIELD

The present invention relates generally to solid phase chemistry. More particularly, the invention relates to an improved method for conducting chemical or biochemical reactions on a substrate surface as may be carried out, for example, in a hybridization assay.

BACKGROUND

Solid phase chemistry involves chemical or biochemical reaction between components in a fluid and molecular moieties present on a substrate surface, e.g., in the synthesis of a surface-bound oligonucleotide or peptide, in the generation of combinatorial "libraries" of surface-bound molecular moieties, and in hybridization assays in which a component present in a fluid sample hybridizes to a complementary molecular moiety bound to a substrate surface. Regardless of the context, all chemical or biochemical reactions between components in a fluid and molecular moieties present on a substrate surface require that there be adequate contact between the fluid's components and the surface-bound molecular moieties. To this end, a number of approaches have been proposed to facilitate mixing of fluid components during solid phase chemical or biochemical reactions so that a substantially homogeneous fluid contacts the reactive surface. Most recently, a great deal of attention has focused on improving hybridization assays using various mixing techniques.

Hybridization reactions between surface-bound molecular probes and target molecules in a sample fluid may be used to detect the presence of particular biomaterials including biopolymers and the like. The surface-bound probes may be oligonucleotides, peptides, polypeptides, proteins, antibodies or other molecules capable of reacting with target molecules in solution. Such reactions form the basis for many of the methods and devices used in the new field of genomics to probe nucleic acid sequences for novel genes, gene fragments, gene variants and mutations. The ability to clone and synthesize nucleotide sequences has led to the development of a number of techniques for disease diagnosis and genetic analysis. Genetic analysis, including correlation of genotypes and phenotypes, contributes to the information necessary for elucidating metabolic pathways, for understanding biological functions, and for revealing changes in genes which confer disease. New methods of diagnosis of diseases, such as AIDS, cancer, sickle cell anemia, cystic fibrosis, diabetes, muscular dystrophy, and the like, rely on the detection of mutations present in certain nucleotide sequences. Many of these techniques generally involve hybridization between a target nucleotide sequence and a complementary probe, offering a convenient and reliable means for the isolation, identification, and analysis of nucleotides.

In biological chip or "biochip" arrays, a plurality of probes, at least two of which are different, are arranged in a spatially defined and physically addressable manner on a substrate surface. Such "biochip" arrays have become an increasingly important tool in the biotechnology industry and related fields, as they find use in a variety of applications, including gene expression analysis, drug screening, nucleic acid sequencing, mutation analysis, and the like. Substrate-bound biopolymer arrays, particularly oligonucleotide, DNA and RNA arrays, may be used in screening studies for determination of binding affinity and in diagnostic applications, e.g., to detect the presence of a nucleic acid containing a specific, known oligonucleotide sequence.

As array density is ever increasing, and the need for faster and more accurate hybridization assays is ongoing, there is currently a great deal of emphasis on improving "mixing" of sample fluid during hybridization and, correspondingly, in maximizing contact between the components of the sample fluid and the entirety of the array surface.

For example, the Affymetrix GeneChip® Fluidics Station hybridization and wash instrument includes a means for pumping a sample fluid back and forth across an array on a substrate surface while the substrate is mounted in a holder. While this method provides for mixing of components within the sample fluid, there are disadvantages that can adversely affect the accuracy of the hybridization reaction. That is, the method is prone to contamination because of the number and variety of materials that come into contact with the sample fluid, i.e., adhesives, various plastic components, and the like. In addition, large sample volumes (greater than 200 µl) are required, and temperature control is poor.

In U.S. Pat. No. 4,849,340 to Oberhardt, an alternative means is disclosed for mixing components in a fluid during an assay performed in an enclosed chamber. Oberhardt discloses an apparatus comprising a base, an overlay and a cover which when combined define a sample well, a channel, and a reaction space. Fluids introduced into the sample well flow by capillary action to the reaction space. Mixing of fluids within the reaction space is effected using mechanical or electromechanical means to create forced convection currents. Again, large sample volumes are required (100 to 200 µl) because of the need to maintain a gap between the base and the cover during mixing. Additionally, the method relies on capillary action to promote fluid flow, and mixing may thus be slow and incomplete, particularly when viscous reagents are used.

U.S. Pat. No. 5,192,503 to McGrath et al. discloses an apparatus for conducting an in situ assay of a tissue section mounted on a slide. A seal member, mounted on a plate, forms a closed periphery and encloses and defines an interior region on the slide that forms a reaction chamber. A plate covers the slide and seal member. The joined plate and slide together form a probe clip. The reaction chamber may comprise a single chamber or two chambers. In the one-chamber embodiment a time-release material, such as gelatin, is applied over the probe, allowing time for reaction of the tissue sample with reagents before the probe is released and thus able to react with the tissue sample. In the two-chamber embodiment, the probe reaction chamber defined by the closed periphery of a first seal member is divided into two regions by a raised portion of the plate, a mixing chamber and a reaction chamber. At least one end of this raised portion does not contact the first seal member, thereby leaving a channel available for fluid flow. Probe compounds placed in the mixing chamber do not mix with the fluid reagents in the reaction chamber until fluid is induced to flow between the two chambers via a channel in a gap left between the raised portion and the seal member. Fluid flow may be induced by rotating the probe clip to a substantially vertical orientation, allowing fluid reagents from the reaction chamber to flow into the mixing chamber and mix with the probe compounds. Re-orienting the probe clip to the horizontal causes the mixed probe and fluid reagent to flow to the reaction chamber for reaction with a tissue section therein. Thus, the position and flow of fluid reagents and probes in the reaction chamber and the mixing chamber is controlled by gravity. Optionally, both gravity-controlled flow and use of a time-release agent such as gelatin may be used at the same time to regulate the mixing of reagent fluids and probes. Like the Oberhardt device, the McGrath et al. apparatus is disadvantageous when viscous solutions are used or rapid mixing is required, insofar as mixing depends upon gravity to induce flow.

Still another method for mixing components in a sample fluid during a solid phase chemical or biochemical reaction is disclosed in commonly assigned, U.S. patent application Ser. No. 09/343,372, now U.S. Pat. No. 6,258,593 to Schembri et al., filed Jun. 30, 1999 ("Apparatus and Method The Conducting Chemical or Biochemical Reactions on a Solid Surface Within an Enclosed Chamber"). That method involves mixing a very thin film of fluid in a chamber, wherein an air bubble is incorporated therein and, when used in hybridization, a surfactant is preferably present as well.

All of the prior methods and devices of which applicants are aware are disadvantageous in one or more respects. Some of the disadvantages have been alluded to in the foregoing discussion. However, the prior art is problematic in other ways as well. For example, there has, until now, been a tradeoff between sample volume and manufacturing flexibility. That is, it is preferable to work with a very small sample volume to in order to increase the precision of the surface chemistry (as, for example, in a hybridization assay). Small sample volumes, however, have in turn meant device miniaturization, requiring extraordinarily precise control over the dimensions of all device components. Furthermore, the majority of hybridization methods and devices involve bringing the sample fluid into contact with the surface-bound probes before the correct hybridization temperature is reached; this means that hybridization will occur at non-optimum conditions, i.e., at a lower temperature, resulting in non-specific binding. In addition, contamination is frequently a problem in devices containing multiple components, and cross-contamination between samples is an additional problem with devices fabricated from non-disposable materials. Finally, sample recovery with prior devices and methods has proved difficult, as the sample fluid must be drawn off of a substrate surface after hybridization, rather than extracted from a container or well.

The present invention is addressed to the aforementioned need in the art, and provides a novel method for conducting a chemical or biochemical reaction on a solid surface as may be done, for example, in the context of a hybridization assay. The novel method provides for numerous advantages relative to the art. For example, the method:

(1) provides effective mixing during solid phase chemical or biochemical reactions and ensures that sample components adequately contact the substrate surface;
(2) allows for use of very small sample volumes without requiring correspondingly small device dimensions and associated manufacturing constraints;
(3) reduces the potential for contamination by employing disposable components and minimizing the number of different materials in contact with the sample fluid;
(4) improves the ease of sample recovery and maximizes the amount of sample fluid that can be recovered; and
(5) enables physical separation of the sample fluid and substrate surface until the desired reaction temperature (e.g., hybridization temperature) is reached.

The invention thus represents a significant advance in the field of solid phase chemistry.

SUMMARY OF THE INVENTION

It is accordingly a primary object of the invention to provide an improved method for conducting chemical or biochemical reactions on a solid surface within an enclosed chamber, such as may be done in a hybridization assay.

It is a further object of the invention to provide such a method in which the chemical or biochemical reactions involve hydrogen bonding, ionic association or covalent attachment of a component in a fluid with molecular moieties present on an interior surface of the enclosed chamber.

It is still a further object of the invention to provide such a method in which the enclosed chamber is present within a mixing device, and wherein, during the chemical or biochemical reaction, centrifugal force is applied to the device.

It is yet a further object of the invention to provide such a method in which, in addition to the centrifugal force, the device is rotated about an axis thereof in a manner effective to maximize contact between the fluid and the entirety of the interior surface on which molecular moieties are present.

It is an additional object of the invention to provide an improved method for conducting a hybridization assay wherein thorough mixing of a sample fluid is ensured and contact between the fluid and surface-bound molecular probes (e.g., as may be present in an array) is maximized.

It is another object of the invention to provide such methods in which contamination is minimized.

It is still another object of the invention to provide such methods wherein the volume of fluid in the chamber is on the order of 10 µl to 20 µl.

Additional objects, advantages and novel features of the invention will be set forth in part in the description which follows, and in part will become apparent to those skilled in the art upon examination of the following, or may be learned by practice of the invention.

In a first aspect of the invention, then, an improved method is provided for conducting a chemical or biochemical reaction between a fluid and a solid surface within an enclosed chamber, wherein the improvement comprises mixing components in the fluid while the fluid contacts the reactive surface by (a) applying centrifugal force to the chamber, e.g., by centrifuging a device containing the chamber using a conventional centrifugation apparatus, and simultaneously (b) rotating the chamber about an axis thereof.

In another aspect of the invention, an improved hybridization assay is provided in which components in a sample fluid hybridize to molecular probes bound to a solid surface within a hybridization chamber, wherein the improvement comprises mixing components in the sample fluid during hybridization by (a) applying centrifugal force to the hybridization chamber, and simultaneously (b) rotating the hybridization chamber about an axis thereof.

DETAILED DESCRIPTION OF THE FIGURES

DETAILED DESCRIPTION OF THE INVENTION

Definitions and Nomenclature

Figure 1:
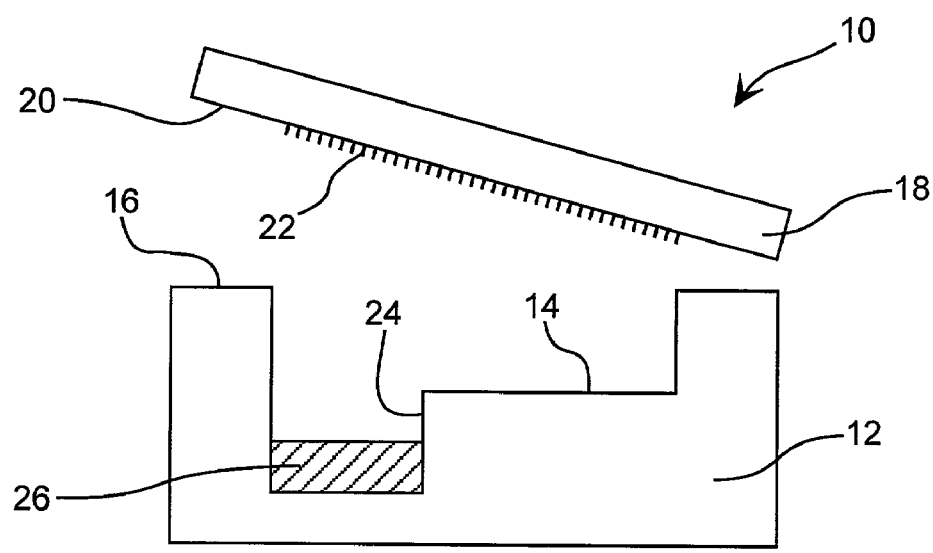
FIG. 1 is a cross-sectional view of a mixing device useful in conjunction with the method of the invention.

Before describing the present invention in detail, it is to be understood that this invention is not limited to specific compositions, reagents, process steps, or equipment, as such may vary. It is also to be understood that the terminology used herein is for the purpose of describing particular embodiments only, and is not intended to be limiting.

It must be noted that, as used in this specification and the appended claims, the singular forms "a," "an" and "the" include plural referents unless the context clearly dictates otherwise. Thus, reference to "a component" includes more than one component, reference to "an array" includes two or more arrays, reference to "a target molecule" includes two or more target molecules, and the like.

In describing and claiming the present invention, the following terminology will be used in accordance with the definitions set out below.

The term "biochip" as used herein means a substrate upon which at least one, and often a plurality, of probe chemicals, such as oligonucleotides, are adherent. The substrates mentioned herein are typically "biochips." A biochip is useful for analysis of sample fluids contacting its surface. Target components of the sample fluid that react with complementary molecular probes on the biochip are thereby able to be detected; biochips with an array of probes thereon allow simultaneous screening of samples for a variety of target components.

The terms "array" and "biomolecular array" are used interchangeably herein to refer to an ordered pattern of molecular probes affixed to a substrate surface and arranged thereon in a spatially defined and physically addressable manner. Such arrays may be comprised of oligonucleotides, peptides, polypeptides, proteins, antibodies, or other molecules used to detect sample molecules in a sample fluid.

The term "target molecule" refers to a known or unknown molecule in a sample, which will hybridize to a molecular probe on a substrate surface if the target molecule and the molecular probe contain complementary regions. In general, the target molecule is a "biopolymer," i.e., an oligomer or polymer such as an oligonucleotide, a peptide, a polypeptide, a protein, an antibody, or the like.

The term "chemically inert" is used herein to mean substantially unchanged by contact with reagents and condition normally involved in solid phase separations, synthesis and screening.

The term "hybridization" as used herein means binding between complementary or partially complementary molecules, as between the sense and anti-sense strands of double-stranded DNA. Such binding is commonly non-covalent binding, and is specific enough that such binding may be used to differentiate between highly complementary molecules and others that are less complementary. Examples of highly complementary molecules include complementary oligonucleotides, DNA, RNA, and the like, which contain a region of nucleotides arranged in the nucleotide sequence that is exactly complementary to a probe; examples of less complementary oligonucleotides include those with nucleotide sequences containing one or more nucleotides not present in a sequence that would be exactly complementary to a probe oligonucleotide.

The term "hybridization solution" as used herein means a solution suitable for use in a hybridization reaction.

The terms "mix" and "mixing" as used herein refer to a process which results in fluid flow within an enclosed volume so as to more uniformly distribute components within the fluid, e.g., after different solutions are combined, after a solution is newly introduced into a volume or after a component of the solution is locally depleted.

The term "oligonucleotide array" as used herein means a pattern of oligonucleotides that are bound to a substrate surface within a reaction area and arranged in a spatially defined and physically addressable manner. Such a pattern may be of any shape, and is commonly rectangular, with probes arranged in mutually perpendicular columns and rows.

The term "probe" as used herein means a molecule of known identity adherent to a substrate.

In one embodiment, then, an improved method is provided for conducting a chemical or biochemical reaction on a solid surface within an enclosed chamber wherein components within a fluid contact and react with molecular moieties present on an interior surface of the chamber, wherein the improvement involves mixing the components within the fluid while the fluid contacts the interior surface of the chamber by both (a) applying centrifugal force to the chamber and, at the same time, (b) rotating the chamber about an axis thereof in a manner effective to maximize contact between the components of the fluid and the entirety of the interior surface. As illustrated in FIG. 1, the chamber is present within a mixing device shown generally at 10, the device comprised of a housing 12 having a recess 14 and an upper peripheral rim 16. A cover plate 18 having an interior surface 20 with said molecular moieties 22 present thereon, is adapted to sealingly contact the rim 16 and enclose the recess 14, forming the chamber. The device is also illustrated in FIG. 2, which provides a perspective view more clearly showing formation of the chamber between cover plate 18 and the recess 14 in housing 12.

The presence of a fluid-retaining well 24 at the base of the recess 14 is optional, although preferred. As illustrated in FIGS. 1 and 2, when the device 10 is upright, the fluid 26 is contained within the well 24 and is thus recoverable therein after the desired solid phase chemistry, e.g., hybridization, is complete. The well is advantageous in facilitating recovery of virtually all of the fluid used, in contrast to prior art systems, particularly hybridization devices, in which the only way to recover fluid after hybridization is to draw it off the array surface, a process that is difficult and necessarily results in loss of a significant fraction of fluid.

Figure 3:
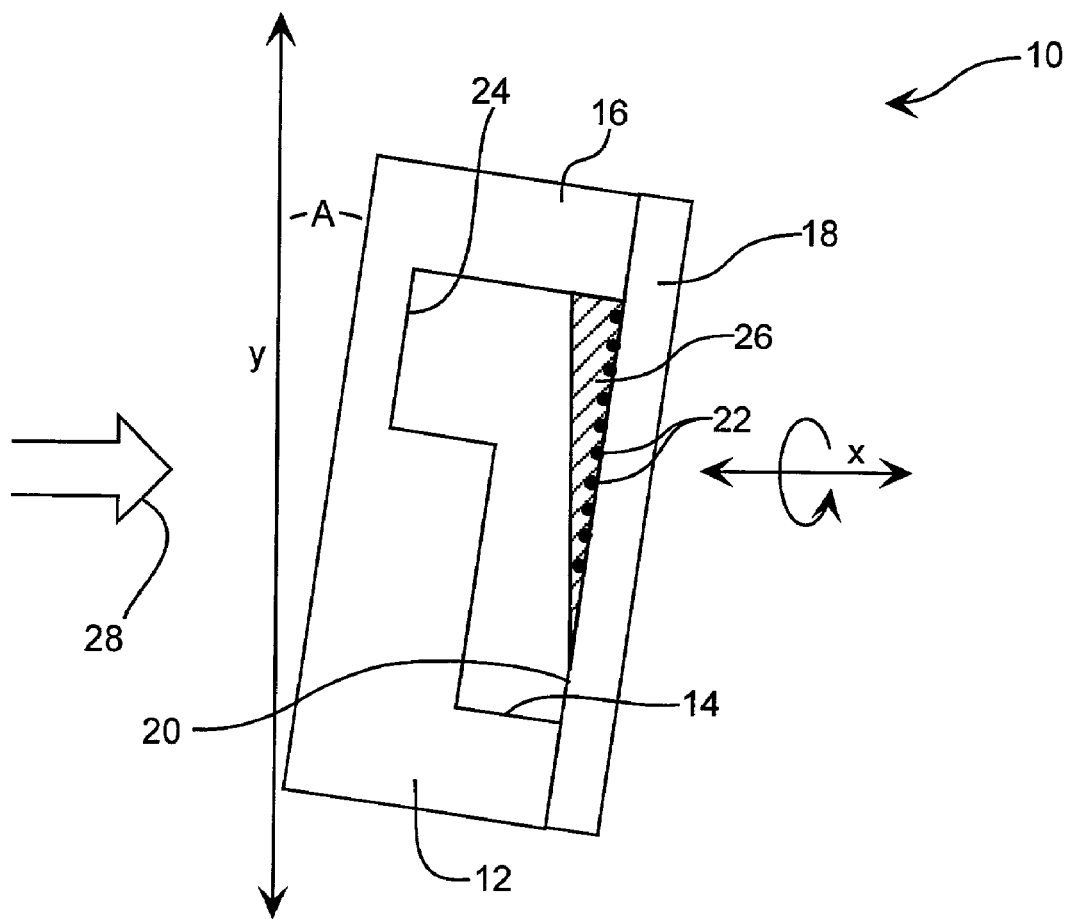
FIG. 3 is a cross-sectional view of the mixing device of FIGS. 1 and 2 shown in use in the method of the invention.

To bring about the desired reaction between the reaction components of fluid 26 and the molecular moieties 22 on the interior surface 20 of cover plate 18, the cover plate is brought into sealing contact with rim 16 and fastened thereto with a fastening means such as a clamp or the like [not shown]. Centrifugal force is then applied along a vector 28 as illustrated in FIG. 3, with the mixing device at an oblique angle A relative to an axis (indicated as y in the figure) that is perpendicular to vector 28. This is typically achieved by appropriately positioning device 10—at the desired degree of tilt—in a centrifugation apparatus, at the periphery thereof, and centrifuging the fluid within the chamber formed between housing 12 and cover plate 18. The centrifugal force applied is typically at least about 1 G, and most preferably is in the range of approximately 10 G to 20 G. During centrifugation, to maximize contact between the reaction components of fluid 26 and the entirety of interior surface 20 having molecular moieties 22 bound thereto, device 10 is additionally rotated about a second axis (indicated as x in FIG. 3), preferably continuously. If desired, the direction of rotation about axis x may be reversed periodically. As illustrated in FIG. 3, movement of fluid 26 along the interior surface 20 is optimized so as to maximize contact between components within the fluid 26 and the surface-bound molecular moieties 22, the movement resulting from not only the oblique positioning of the device but also the simultaneous rotation and application of centrifugal force.

Figure 2:
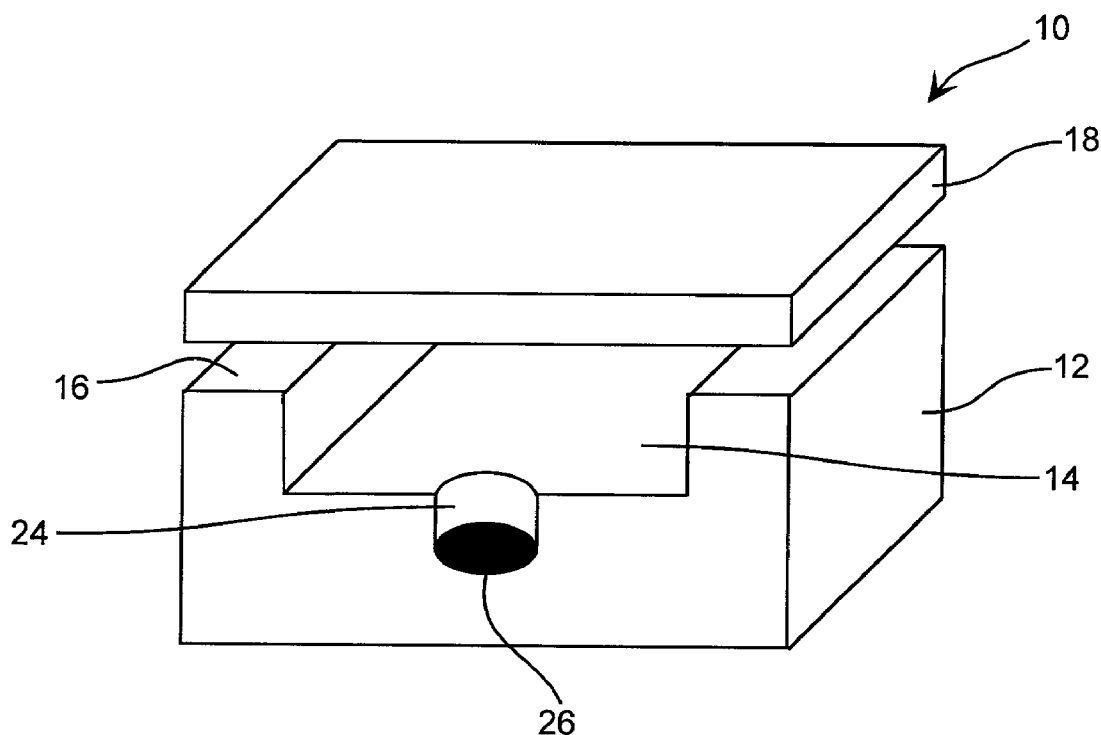
FIG. 2 is a perspective view of the mixing device illustrated in FIG. 1.

The aforementioned system minimizes contamination of reaction components by limiting the materials that come into contact with the fluid; that is, as illustrated in FIGS. 1–3, the fluid 26 contacts only (1) the interior surface 20 of the cover plate 18, and (2) the plastic material used for the housing 12. Prior systems, as alluded to earlier herein, allow a sample fluid to contact a relatively large number of parts and materials, increasing the risk of contamination and, as a result, decreasing the precision of the chemical or biochemical process, e.g., the selectivity and specificity of a hybridization assay. Also, the device used in the present method may be fabricated entirely from disposable materials, eliminating any contamination that could come about from re-use of parts and materials.

Furthermore, the present method and system enables use of a very small volume of fluid, which, as noted earlier herein, is desirable in hybridization assays. However, the reaction (e.g., hybridization) chamber within the mixing device used herein is not required to be of corresponding dimensions. That is, the volume of the chamber may be significantly greater than the amount of fluid used in the reaction, hybridization assay, or the like. Thus, the invention eliminates the need for small device dimensions and associated manufacturing constraints. Additionally, the present method and system allow for the fluid and reactive surface to be heated to the appropriate reaction temperature before the fluid actually contacts the surface. That is, referring now to FIG. 1, the fluid 26 may be introduced into the well 24 (e.g., by pipetting or the like) and the cover plate 18 then positioned so as to close the chamber. The device may then be heated, e.g., to a suitable hybridization temperature, prior to placement in a centrifugation device and application of centrifugal force, wherein, as may be seen in FIG. 3, the fluid 26 then contacts the interior surface 20 of the cover plate. Prior systems involve introduction of a sample fluid into a chamber wherein the surface-bound molecular probes or the like are present on a surface at the base of the chamber, such that the sample fluid contacts the probes before the device can be heated to a suitable hybridization chamber. The present method thus provides a significant advantage relative to the art, and substantially reduces the occurrence of nonspecific hybridization which can result at lower temperatures.

Figure 4:
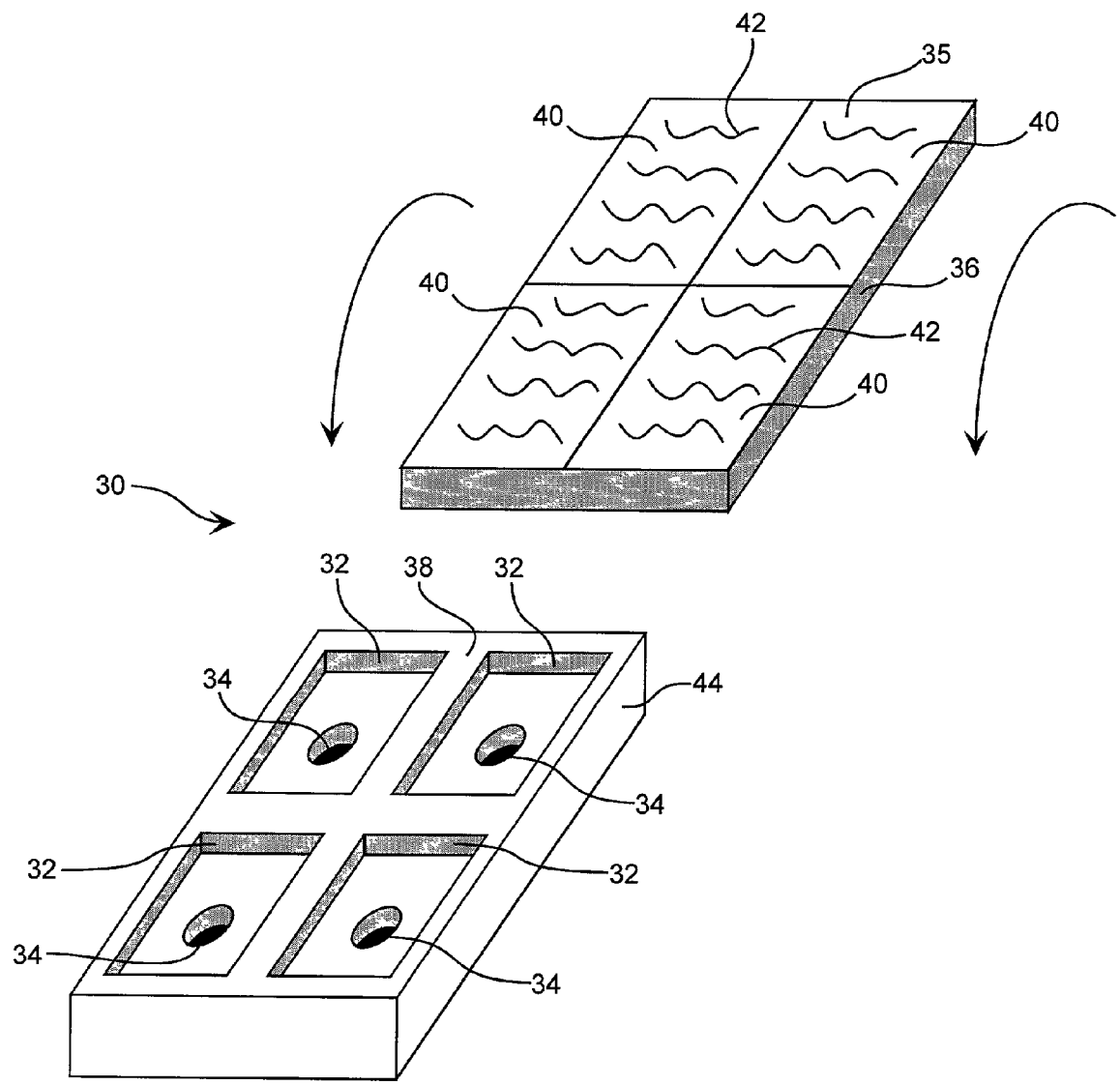
FIG. 4 is a perspective view of an alternative mixing device useful in conjunction with the method of the invention, wherein a plurality of reaction (e.g., hybridization) chambers are present in a single housing.
Figure 5:
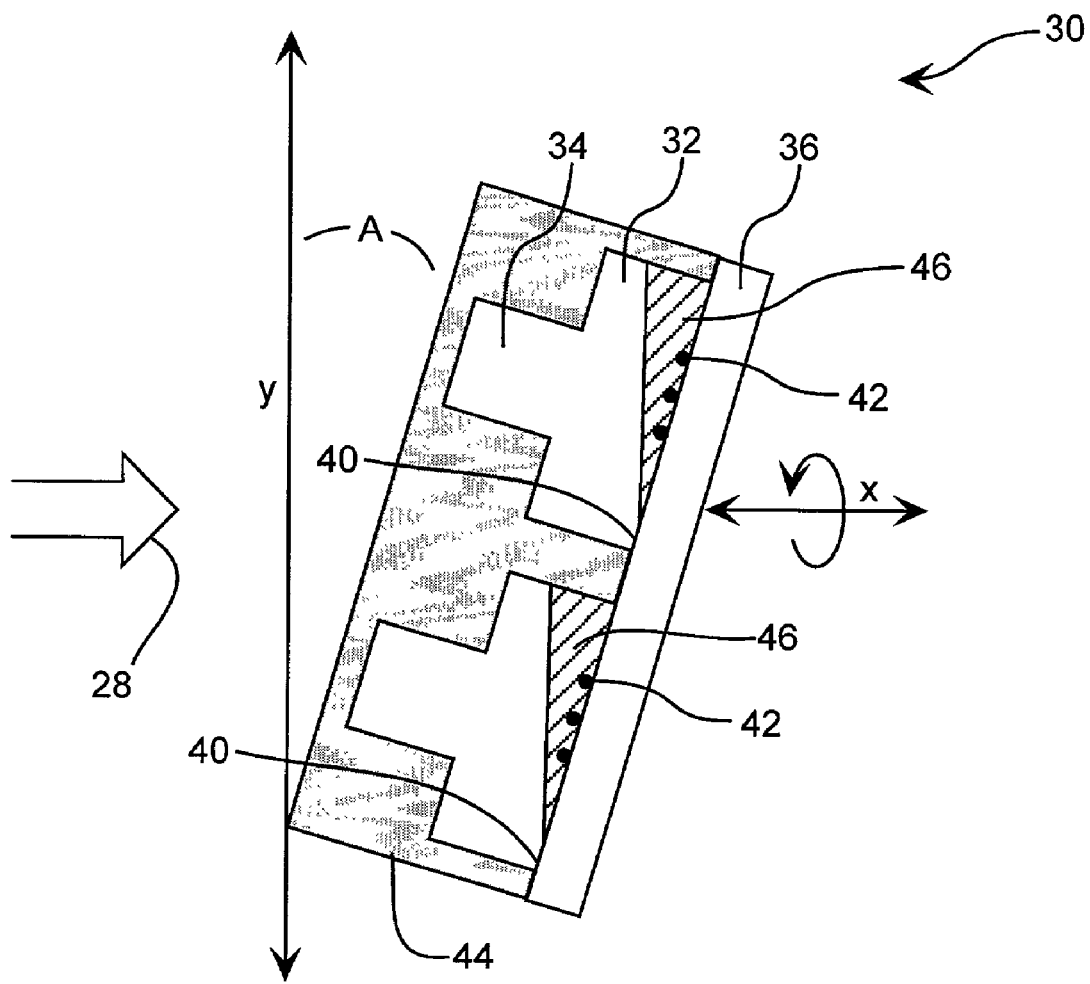
FIG. 5 is a cross-sectional view of the mixing device of FIG. 4 shown in use in the method of the invention.

In an alternative embodiment, illustrated in FIG. 4, a mixing device 30 comprises a housing 44 with a rim 38 and a plurality of recesses 32 therein; in this embodiment also, although optional, it is preferred that fluid-containing wells 34 be present at the base of each recess 32. Enclosed chambers are formed upon sealing placement of cover plate 36 on the rim 38 of the housing 44, wherein a different solid phase chemical or biochemical reaction may be carried out in each of said chambers. The interior surface 35 of cover plate 36 is divided into a plurality of regions 40 each having molecular moieties 42 bound thereto, wherein each region 40 is adapted to cover a corresponding recess 32. In FIG. 5, the mixing device 30 comprising housing 44 and cover plate 36 is shown positioned at an oblique angle A relative to the direction of applied centrifugal force 28, and rotation about the axis x facilitates mixing of components within the fluid 46 and maximizes contact between the fluid 46 and the interior surface regions 40 with molecular moieties 42 bound thereto.

Figure 6:
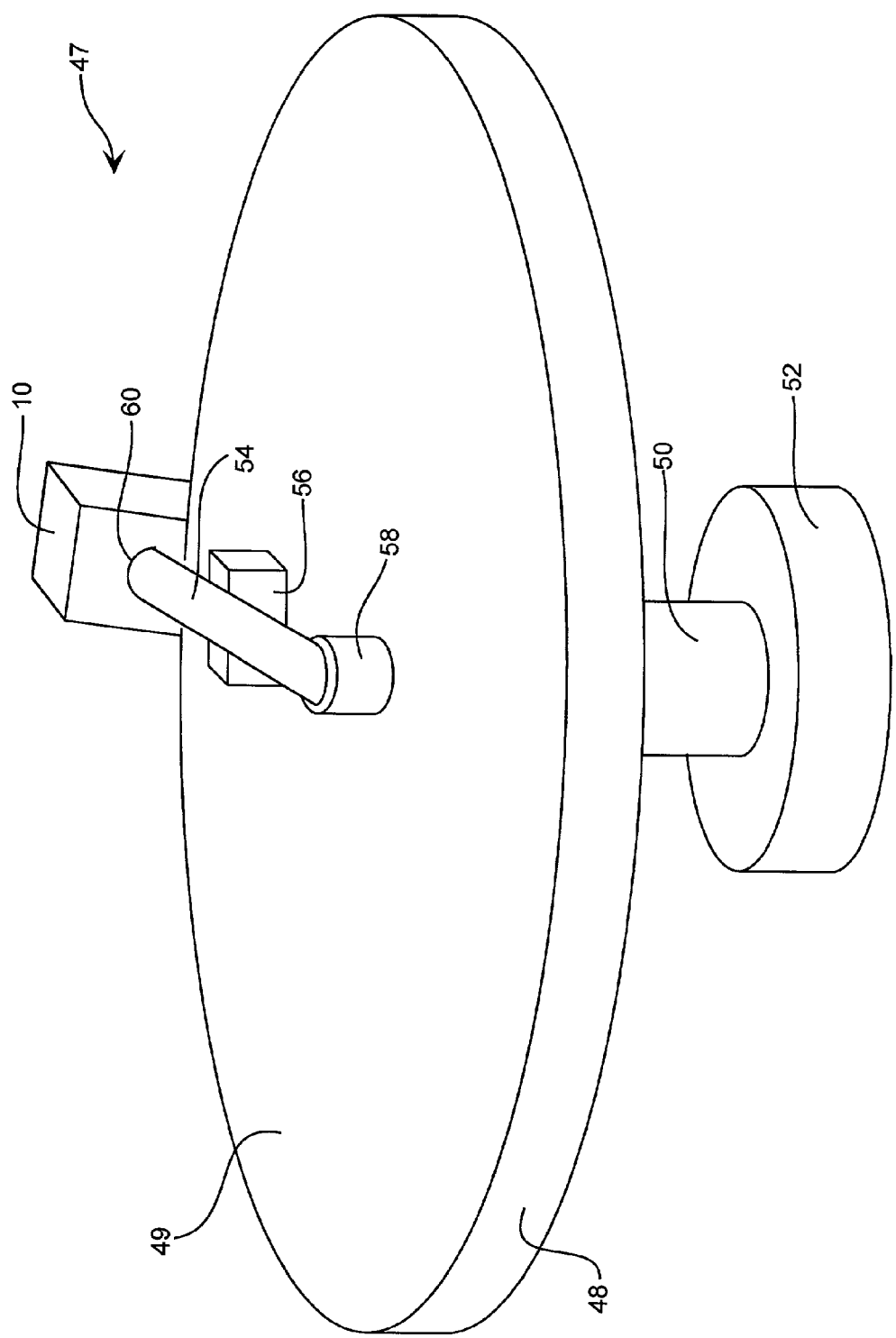
FIG. 6 is a perspective view illustrating positioning of a mixing device as provided herein within a centrifuge apparatus.

FIG. 6 illustrates the above-mentioned devices in place on a centrifugation device 47 in which the centrifuge rotor 48 is coupled directly or indirectly via shaft 50 to a motor 52 for rotating the rotor about an axis of rotation. On the upper surface 49 of the rotor 48 is a radially positioned arm 54 (shown supported by block 56) operably connected by way of a control means 58 to shaft 50, with a mixing device 10 (or alternatively mixing device 30) as described hereinabove positioned at the distal terminus 60 of the arm and locked into place via a fastening means such as a mounting bracket or the like (not shown). The central control means 58 enables the mixing device 10 to be tilted or otherwise moved about an axis, e.g., rotated during centrifugation.

In a preferred embodiment, the method is used to facilitate mixing and surface-sample interaction in a hybridization assay. In this embodiment, the molecular moieties bound to the interior surface of the cover plate are molecular probes. Preferably, the molecular probes are arranged in a spatially defined and physically addressable manner, i.e., are present in one or more "arrays." In a most preferred embodiment, the probes are oligonucleotide probes (including cDNA molecules or PCR products), although other biomolecules, e.g., oligopeptides and the like, may serves as probes as well.

It is preferred that the housing be made of plastic and the cover plate of glass, plastic, fused silica or silicon, the seal between plastic and either glass, plastic, fused silica or silicon being advantageous. The housing material should be thermally stable, chemically inert, and preferably non-stick. Furthermore, when the apparatus is used in hybridization, the housing should be comprised of a material that is chemically and physically stable under conditions employed in hybridization. In a preferred embodiment, the plastic housing is polypropylene, polyethylene or acrylonitrile-butadiene-styrene ("ABS"). In the most preferred embodiment, the housing is comprised of polypropylene. The housing may be constructed by machining or molding technologies.

The invention is particularly useful in conjunction with substrate surfaces functionalized with silane mixtures, as described in copending, commonly assigned U.S. patent application Ser. No. 09/145,015, filed Sep. 1, 1998, now U.S. Pat. No. 6,258,454, and entitled "Functionalization of Substrate Surfaces with Silane Mixtures." That method provides a functionalized surface on a substrate with low surface energy. The method for preparing such a surface comprises contacting a substrate having reactive hydrophilic moieties on its surface with a derivatizing coniposition comprising silane-containing groups $R^1$—$Si(R^L R^x R^y)$ and $R^2$-$(L)_n$-$Si(R^L R^x R^y)$ under reaction conditions effective to couple the silanes to the substrate. This provides —Si—$R^1$ and —Si-(L)$_n$-R$^2$ groups on the substrate, The R$^L$, which may be the same or different, are leaving groups, the R$^x$ and R$^y$ which may also be the same or different, are either leaving groups, like R$^L$ or are lower alkyl, R$^1$ is a chemically inert moiety that upon bluffing to the substrate surface lowers the surface energy thereof, n is 0 or 1, L is a linking group, and R$^2$ comprises either a functional group enabling covalent binding of a molecular moiety or a group that may be modified to provide such a functional group. The ratio of the silanes in the derivatizing composition determines the surface energy of the functionalized substrate and the density of molecular moieties that can ultimately be bound to the substrate surface. When used in conjunction with the present invention, the surface-bound molecular probes are bound to the R$^2$ moieties provided by the second silane-containing group.

It is to be understood that while the invention has been described in conjunction with the preferred specific embodiments thereof, the description above is intended to illustrate and not limit the scope of the invention. Other aspects, advantages and modifications within the scope of the invention will be apparent to those skilled in the art to which the invention pertains.

The invention claimed is:

1. A method for contacting a fluid with an interior surface of a closed chamber, wherein said interior surface comprises molecular moieties bound thereto in a spatially defined and addressable manner, comprising;

providing the fluid in the chamber and applying centrifugal force ranging from about 1 G to about 20 G to the fluid in the chamber by rotating said chamber about a first axis while simultaneously rotating the chamber about a second axis thereof in a manner effective to vary the amount of fluid contacting any one point on the interior surface, wherein the chamber is contained within a mixing device comprised of (a) a housing having a recess and a rim, and (b) a cover plate having an interior surface with said molecular moieties present thereon, wherein the cover plate sealingly contacts the rim and encloses the recess, forming said chamber.

2. The method of claim 1, wherein the device further comprises a fluid-retaining well at the base of the recess, whereby after completion of mixing and placement of the device in an upright position, the fluid is recovered in the well.

3. The method of claim 1, wherein the centrifugal force is applied by positioning the device in a centrifugation apparatus and centrifuging the fluid within the chamber.

4. The method of claim 3, wherein the device is positioned in the centrifugation apparatus at an angle such that the cover plate is not perpendicular to said first axis.

5. The method of claim 1, wherein the molecular moieties are molecular probes.

6. The method of claim 1, wherein the molecular probes are oligonucleotide probes.

7. The method of claim 1, wherein the molecular probes are polypeptide probes.

8. The method of claim 1, wherein the housing is comprised of a material that is chemically and physically stable under conditions employed in hybridization assays.

9. The method of claim 8, wherein the housing is comprised of a material that is thermally stable at temperatures of at least about 50° C.

10. The method of claim 8, wherein the housing is comprised of a material that is chemically inert.

11. The method of claim 8, wherein the housing is comprised of a material selected from the group consisting of polypropylene, polyethylene and acrylonitrile-butadiene-styrene.

12. The method of claim 1, wherein the cover plate is comprised of glass.

13. The method of claim 1, wherein the interior surface of the cover plate is functionalized with a mixture of a first silane providing surface —Si—R$^1$ groups where R$^1$ is a chemically inert moiety and a second silane providing surface —Si-(L)$_n$-R$^2$ groups where L is a linking group, n is 0 or 1, and R$^2$ is a functional group covalently attached to said molecular moieties.

14. The method of claim 1, wherein the amount of fluid within the enclosed chamber is in the range of approximately 10 µl to 20 µl.

15. The method of claim 1, wherein the direction of said simultaneous rotation is periodically reversed.

16. The method of claim 1, wherein the enclosed chamber is contained within a mixing device comprising two or more enclosed chambers.

17. The method of claim 16, wherein the mixing device is comprised of (a) a housing having at least two recesses and a rim, and (b) a cover plate having an interior surface with said molecular moieties present thereon, wherein the cover plate sealingly contacts the rim and encloses the recesses, forming said chambers.

18. The method of claim 17, wherein the mixing device further comprises a fluid-retaining well at the base of each recess, whereby after completion of mixing and placement of the device in an upright position, the fluid is recovered in each well.

19. A method for contacting an interior surface of a chamber during hybridization, wherein said interior surface comprises oligonucleotide probes bound thereto in a spatially defined and addressable manner, comprising:

providing the fluid in the chamber and applying centrifugal force ranging from about 1 G to about 20 G to the fluid in the chamber by rotating the chamber about a first axis while simultaneously rotating the chamber about a second axis thereof in a manner effective to vary the amount of fluid contacting any one point on the interior surface during the hybridization, wherein the hybridization chamber is contained within a hybridization device comprised of (a) a housing having a recess and a rim, and (b) a cover plate having an interior surface with said oligonucleotide probes present thereon, wherein the cover plate sealingly contacts the rim and encloses the recess, forming said hybridization chamber.

20. The method of claim 19, wherein the sample fluid further comprises a hybridization buffer.

21. The method of claim 19, wherein the hybridization device further comprises a fluid-retaining well at the base of the recess, whereby after placement of the device in an upright position, the fluid is recovered in the well.

22. The method of claim 19, wherein the centrifugal force is applied by positioning the hybridization device in a centrifugation apparatus and centrifuging the sample fluid within the hybridization chamber.

23. The method of claim 22, wherein the hybridization device is positioned in the centrifugation apparatus at an angle such that the cover plate is not perpendicular to the axis defined by the vector along which centrifugal force is applied.

24. The method of claim 19, wherein the housing is comprised of a material that is chemically and physically stable under conditions employed in hybridization assays.

25. The method of claim 24, wherein the housing is comprised of a material that is thermally stable at temperatures of at least about 50° C.

26. The method of claim 24, wherein the housing is comprised of a material that is chemically inert.

27. The method of claim 24, wherein the housing is comprised of a material selected from the group consisting of polypropylene, polyethylene and acrylonitrile-butadiene-styrene.

28. The method of claim 24, wherein the cover plate is comprised of glass.

29. The method of claim 24, wherein the interior surface of the cover plate is functionalized with a mixture of a first silane providing surface —Si—$R^1$ groups where $R^1$ is a chemically inert moiety and a second silane providing surface —Si-$(L)_{n-R}^2$ groups where L is a linking group, n is 0 or 1, and $R^2$ is a functional group covalently attached to said oligonucleotide probes.

30. The method of claim 19, wherein the amount of sample fluid within the hybridization chamber is in the range of approximately 10 µl to 20 µl.

31. The method of claim 19, wherein the direction of said simultaneous rotation is periodically reversed.

32. The method of claim 19, wherein the hybridization chamber is contained within a hybridization device comprising two or more hybridization chambers.

33. The method of claim 32, wherein the hybridization device is comprised of (a) a housing having at least two recesses and a rim, and (b) a cover plate having an interior surface with said oligonucleotide probes present thereon, wherein the cover plate sealingly contacts the rim and encloses the recesses, forming said hybridization chambers.

34. The method of claim 33, wherein the hybridization device further comprises a fluid-retaining well at the base of each recess, whereby after placement of the device in an upright position, the fluid is recovered in each well.

* * * * *

UNITED STATES PATENT AND TRADEMARK OFFICE
CERTIFICATE OF CORRECTION

PATENT NO. : 7,045,287 B2
APPLICATION NO. : 09/792169
DATED : May 16, 2006
INVENTOR(S) : Smith et al.

It is certified that error appears in the above-identified patent and that said Letters Patent is hereby corrected as shown below:

In column 9, line 29, in Claim 1, after "comprising" delete ";" and insert -- : --, therefor.

In column 11, line 19, in Claim 29, delete "-Si-$(L)_{n-R}{}^2$" and insert -- -Si-$(L)_n$-$R^2$ --, therefor.

Signed and Sealed this

Twenty-eighth Day of November, 2006

JON W. DUDAS
*Director of the United States Patent and Trademark Office*